United States Patent [19]

Crump et al.

[11] Patent Number: 5,208,363

[45] Date of Patent: May 4, 1993

[54] PREPARATION OF AMINONITRILES

[75] Inventors: Druce K. Crump, Lake Jackson; David A. Wilson, Richwood, both of Tex.

[73] Assignee: The Dow Chemical Company, Midland, Mich.

[21] Appl. No.: 878,572

[22] Filed: May 5, 1992

Related U.S. Application Data

[63] Continuation-in-part of Ser. No. 597,625, Oct. 15, 1990, abandoned.

[51] Int. Cl.$^5$ .......................................... C07C 253/30
[52] U.S. Cl. ..................................................... 558/346
[58] Field of Search ........................................ 558/346

[56] References Cited

U.S. PATENT DOCUMENTS

| | | | |
|---|---|---|---|
| 2,205,995 | 6/1940 | Ulrich et al. | 558/346 |
| 2,405,966 | 8/1946 | Loder | 558/346 |
| 2,407,645 | 9/1946 | Bersworth | 558/346 |
| 2,731,490 | 1/1956 | Barsky | 558/346 X |
| 2,855,428 | 10/1958 | Singer et al. | 558/346 |
| 2,860,164 | 11/1958 | Kroll et al. | 558/346 X |
| 2,890,238 | 6/1959 | Sexton | 558/346 X |
| 3,424,783 | 1/1969 | Harper et al. | 558/346 |
| 3,463,805 | 7/1969 | Morgan et al. | 558/346 |
| 3,515,742 | 6/1970 | Morgan et al. | 558/346 |
| 3,644,444 | 2/1972 | Popper et al. | 558/346 X |
| 3,679,729 | 7/1972 | Daniels | 558/346 |
| 3,714,223 | 1/1973 | Godfrey et al. | 558/346 |
| 3,758,534 | 9/1973 | Popper et al. | 260/429 |
| 3,907,858 | 9/1975 | Davis et al. | 558/346 |
| 3,925,448 | 12/1975 | Tanier | 558/346 |
| 3,959,342 | 5/1976 | Homberg et al. | 558/346 |
| 3,988,360 | 10/1976 | Gaudette et al. | 558/346 |
| 4,022,815 | 5/1977 | Schlecht et al. | 558/346 |
| 4,478,759 | 10/1984 | Diatler et al. | 558/346 |
| 4,560,516 | 12/1985 | Singer | 558/346 |
| 4,661,614 | 4/1987 | Most et al. | 558/346 |
| 4,704,465 | 11/1987 | Tannet et al. | 558/346 |
| 4,980,471 | 12/1990 | Christiansen et al. | 544/384 |

OTHER PUBLICATIONS

Stewart, et al., J. Chem. Soc., pp. 3281–3285, (1940), vol. 62.
Choh-Hao Li, et al., J. Chem. Soc., pp. 2596–2599, (1937), vol. 59.
Stewart, et al., J. Chem. Soc., pp. 2782–2787, (1938), vol. 60.

*Primary Examiner*—Joseph Paul Brust

[57] ABSTRACT

The present invention is a process for preparing aminoacetonitriles or ethylenediamine tetraacetonitrile comprising the steps of (a) admixing glycolonitrile with an amine having at least one primary amine group or ethylenediamine to form an intermediate amine acetonitrile reaction product, (b) admixing the reaction product of Step (a) with formaldehyde and hydrocyanic acid such that each hydrogen on an amine nitrogen is replaced by an acetonitrile group. The resulting aminoacetonitrile advantageously has all amino groups fully substituted with acetonitrile groups.

28 Claims, No Drawings

PREPARATION OF AMINONITRILES

CROSS REFERENCE TO RELATED APPLICATION

This application is a continuation-in-part of application Ser. No. 597,625, filed Oct. 15, 1990, now abandoned.

Aminonitriles are useful, for instance, in preparing aminocarboxylic acid compounds. For example, ethylenediaminetetraacetonitrile can be hydrolyzed to prepare ethylenediaminetetraacetic acid (EDTA). Processes for the hydrolysis are known in the art, as exemplified by the teachings in U.S. Pat. Nos. 2,407,645; 2,164,781; and 2,205,995.

Aminonitriles, also known as aminocarboxylic acid nitriles, have been prepared in a number of ways, often from certain amines reacted with certain carbonyl compounds, particularly formaldehyde and hydrocyanic acid (hydrogen cyanide, HCN). For instance, U.S. Pat. No. 2,205,995 (Ulrich, et al.), a process involves a reaction of certain amine salts with certain carbonyl compounds and hydrocyanic acid prepared from acidified cyanide salts. Ethylenediaminetetraacetonitrile is among the compounds prepared. Similarly, in U.S. Pat. No. 2,407,645, Bersworth discloses a process for preparing certain polycarboxylic amino acids from certain aliphatic amines reacted with formaldehyde and an alkali metal cyanide. In U.S. Pat. No. 4,855,428, Singer teaches yet another process in which certain amines are fed into a reaction medium containing formaldehyde and hydrocyanic acid. The medium is acidified and remains liquid. In U.S. Pat. No. 3,424,783 Harper et al. teach reacting an amine with formaldehyde and hydrocyanic acid in the presence of an aqueous slurry of acidic ionic exchange resin to produce certain aminonitriles. In U.S. Pat. Nos. 3,463,805 and 3,515,742 Morgan et al. emphasize characteristics of adiabatic conditions in reacting certain amines with formaldehyde and hydrocyanic acid in the presence of certain acidic catalyst. More recently, in U.S. Pat. No. 4,478,759, Distler et al. disclose a process for reacting certain nitrogen compounds with formaldehyde and hydrocyanic acid in the presence of additional acids such that the pH is less than about 2 and temperatures are from about 10° C. to about 70° C. The concentration of hydrocyanic acid is controlled carefully. In U.S Pat. No. 4,704,465 Lannert et al. disclose a process for combining formaldehyde with ethylenediamine under certain conditions. A two-stage process is taught in U.S. Pat. No. 4,560,516 (Singer). Other disclosures of reactions of certain amines with formaldehyde and hydrocyanic acid include, U.S. Pat. Nos. 3,644,444 (Popper et al.); 3,679,729 (Daniels); 3,714,223 (Godfrey et al); 3,758,534 (Popper eta al.); and 3,988,360 (Gaudette et al.). Additionally, formaldehyde and hydrocyanic acid are reacted with ammonia to produce nitrilotriacetonitrile by processes such as those disclosed in U.S. Pat. Nos. 3,907,858 (Davis et al.); 3,925,448 (Lanier) and 3,959,342 (Homberg et al.).

In some instances glycolonitrile (also known as glyconitrile and hydroxyacetonitrile) has been reacted with amines. For instance, in U.S. Pat. No. 2,861,164 Kroll discloses certain carboxymethylations of certain amines by reacting glycolonitrile with primary or secondary amines in an aqueous solution at temperatures greater than about 85° C. to the boiling point of the mixture in the presence of basic hydroxides of alkali metals or alkaline earth metals or quaternary ammonium hydroxide to achieve carboxymethylation of the amine. In Column 2, lines 48-51 of this patent, Kroll discloses previous reactions of glycolonitrile with amines where reactions at primary amines are limited to reaction of the first hydrogen on each nitrogen.

SUMMARY OF THE INVENTION

The present invention is a process for preparing amino acetonitriles comprising the steps of: (a) reacting by contacting in a liquid aqueous reaction medium, at a basic pH and at a temperature of from about 0° C. to about 70° C. glycolonitrile with an unsubstituted or inertly-substituted amine having at least one primary amine group to form an intermediate aminonitrile, (b) placing the reaction product of Step (a) in a suitable acidic liquid reaction medium at a temperature of from about 0° C. to about 90° C. and thereafter admixing it with formaldehyde and hydrocyanic acid such that each hydrogen on an amine nitrogen is replaced by an acetonitrile group.

The insoluble, fully-substituted aminonitrile can be then saponified using processes known in the art as described in U.S. Pat. Nos. 2,407,645 (Bersworth), 2,164,781 (Platz) and 2,205,995 (Ulrich) to form aminotetraacetic acid.

DETAILED DESCRIPTION OF THE INVENTION

Amines suitable for the process of the invention are amines having at least one primary amine group. The amines preferably have from about 2 to about 20 carbon atoms and preferably have at least about 2 amine groups, more preferably from about 2 to about 4 amine groups. Of these amine groups, at least one is primary, preferably at least 2 are primary, most preferably about 2 amine groups per molecule are primary amine groups.

The amine preferred for this process is ethylenediamine (EDA), while other amines may be used. Amines are commercially available or may be prepared by processes within the skill in the art such as by 1) the reaction of ammonia with alkyl halides (with and without catalysts), 2) catalytic amination of alcohols or amino alcohols, or 3) catalytic reduction of nitriles.

The amines are unsubstituted or inertly substituted, that is, substituted with groups which do not undesirably interfere with the reaction steps of the invention. Such inert substitution includes, for instance, hydroxyalkyl groups, carboxylic acid groups, sulfonic acid groups, and phosphonic acid groups. However, substitution is generally not desirable since the solubility in water may be increased. Increased solubility impairs isolation of the nitrile product.

The amine is admixed with glycolonitrile which is commercially available and is obtained by the reaction of HCN with formaldehyde which is within the state of the art such as illustrated by U.S. Pat. Nos. 2,731,490 and 2,890,238.

Preferred ratios of glycolonitrile to amine in the first step depend on the amine. For example, with ethylenediamine (EDA), the most preferred ratio is one mole of EDA to 1.9 to 2.0 moles of glycolonitrile. In the case of diethylenetriamine, about 2.8 to 3.0 moles of glycolonitrile are most preferably used with one mole of the amine. In general, the amount of glycolonitrile used is preferably less than or equal to an equivalent amount based on primary and secondary amine nitrogens of the amine. A primary amino group will accept one glycolonitrile addition, but under the preferred conditions for the reaction a second acetonitrile group is not conveniently added using glycolonitrile. Glycolonitrile does add to secondary alkyl amines, such as the secondary amino group of diethylenetriamine. Thus the equivalent amount of glycolonitrile for an amine having one primary and one secondary amine is two equivalents of glycolonitrile. Quantities of glycolonitrile greater than the number of equivalents of primary and secondary amine groups are generally disadvantageous because color and impurities are observed. More preferably, the ratio is about 0.95 to about 0.99 percent of the theoretical equivalents that can be added, to avoid unwanted color.

The reaction of amine and glycolonitrile is suitably carried out at a pH sufficient to allow the glycolonitrile to react with the amine, that is a pH sufficiently high that the amine groups are not protonated, that is preferably a basic pH above about 8, more preferably from about 8 to about 14, most preferably from about 9 to about 13, even more preferably from about 10 to about 12.5. The amine reactant is generally sufficiently basic to achieve the preferred pH in a reaction medium of amine and glycolonitrile. Alternatively, the pH is adjusted prior to or during the reaction using any basic material which does not interfere undesirably with the reaction, e.g. sodium hydroxide. Additional basic materials are generally disadvantageous in that such materials are advantageously neutralized for the reaction with hydrocyanic acid. When, however, the amine is insufficiently basic to result in a reaction mixture of the preferred basicity, such as when the amine has an acidic group, e.g. glycine, additional basic materials are advantageously used.

The reaction is suitably carried out under any conditions under which the amino hydrogens react with the glycolonitrile, batch wise or, advantageously, continuously. The reaction temperature is preferably from about 0° C. to about 70° C., even more preferably from about 5° C. to about 70° C., most preferably from about 10° C. to about 60° C. The reaction can be conducted under reduced pressure, atmospheric pressure or superatmospheric pressure.

The reaction preferably is carried out in the presence of water, more preferably in aqueous solution. The total amount of water is suitably any amount which allows solubility of the reaction product of amine and glycolonitrile and which also does not interfere undesirably with subsequent reaction steps, preferably from about 10 to about 90, more preferably from about 15 to about 50 percent by weight water, based on the total weight of amine and glycolonitrile reaction mixture.

The reaction mixture for the reaction of the primary amine groups, thus, comprises amine, glycolonitrile and, preferably, water. A solvent for the amine and/or glycolonitrile other than water is optionally used instead of the water or with the water. Preferably the solvent is one which dissolves both amine and glycolonitrile such as methanol, ethanol, or other aliphatic alcohol with four or fewer carbon atoms. Use of solvents other than water generally involve use of purification methods other than precipitation of a solid product because the product is often soluble in such solvents. The reaction is, thus, preferably carried out in the presence of water.

The glycolonitrile reacts primarily with any secondary amine group and with one hydrogen on each primary amino group to form a reaction product having at least one secondary amine hydrogen remaining available for subsequent reaction. When it is desired that the remaining hydrogens (on amino groups having an acetonitrile group from the first reaction) be reacted to form an additional acetonitrile group, that reaction is carried out by reaction of the remaining hydrogens present on the amine with hydrocyanic acid and formaldehyde to form a fully derivatized polycarboxylic acid nitrile.

Conveniently, an aqueous solution of glycolonitrile is admixed with an amine for a time sufficient for the reaction to reach a predetermined degree of completeness, which is more preferably substantially complete reaction. Then, preferably, the resulting intermediate aminonitrile is acidified before addition of subsequent reactants. In the case of ethylenediamine, the intermediate aminonitrile is ethylenediamine diacetonitrile (EDDN).

The reaction mixture is preferably adjusted to a pH of less than about 5, more preferably of from about 0 to about 3, most preferably from about 0.5 to about 1. This pH is typically maintained at about pH 1 by addition of a mineral acid such as sulfuric acid, phosphoric acid, or hydrochloric acid as needed.

Then, the acidic mixture of the intermediate aminoacetonitrile is admixed with formaldehyde and hydrocyanic acid (hydrogen cyanide, HCN) under reaction conditions such that each hydrogen on an amine nitrogen is replaced by an acetonitrile group. Advantageously, formaldehyde and hydrocyanic acid are added to the reaction mixture simultaneously. The hydrocyanic acid may be added at a rate appropimately equal to the rate that it is reacted so long as the free hydrocyanic acid is less than 1 percent. In the case of ethylenediamine, the resulting product is ethylenediamine tetraacetonitrile.

Formaldehyde is commercially available and is suitably used in any form such as a liquid or a solid and is preferably used in the form of an aqueous solution, preferably of a strength of from about 20 to about 60 percent by weight, more preferably from about 35 to about 50 percent by weight formaldehyde. The formaldehyde is preferably used in any amount that will essentially completely substitute the remaining amino hydrogens during the reaction with HCN under reaction conditions, preferably in a ratio of about 0.95 to about 1.2 moles of formaldehyde to moles of remaining reactive amino hydrogens on the partially reacted amine. These mole ratios are preferred because it is generally desirable to fully substitute the amino hydrogens with amino acetonitrile groups to form an insoluble product and to minimize the partially substituted amine products in the reaction mixture.

Hydrogen cyanide is commercially available and is suitably used as a gas or, advantageously, as a liquid (either as a solution or pressurized sufficiently to result in a liquid). It is preferably introduced as a concentrated aqueous liquid or in pure liquid form. Slow addition (approximately equal to the rate at which it is reacted under reaction conditions) is desirable to avoid excess free cyanide in the reaction mixture. Thus, the concentration of unreacted hydrogen cyanide in a reaction mixture is preferably from about 0 to about 2, more preferably from 0.01 to about 1.5, most preferably from about 0.01 to about 1 percent by weight based on total weight of the reaction mixture. The hydrogen cyanide is preferably used in an equivalent ratio of from about 0.80 to about 1.2 based on equivalents of remaining amino hydrogens, more preferably an equivalent ratio of from about 0.9 to about 1.15, most preferably from about 0.95 to about 1.1. These ranges are preferred because full aminoacetonitrile substitution is desired, yet excess unreacted HCN in the reaction medium is not desirable.

Any reaction conditions under which the hydrocyanic acid and formaldehyde react with the remaining amine hydrogens of the reaction product of the glycolonitrile and amine are suitable. Preferably, the reaction is carried out from about 0° C. to about 90° C., more preferably from about 25° C. to about 80° C., most preferably from about 30° C. to about 70° C. under reduced pressure, atmospheric pressure or superatmospheric pressure, batch wise or, continuously. The reaction is preferably carried out in the presence of water, introduced from the reaction mixture of glycolonitrile with the amine; water is also introduced as aqueous formaldehyde solution and/or aqueous hydrogen cyanide. The total amount of water is preferably from about 20 to about 90, more preferably from about 30 to about 80, most preferably from about 40 to about 75 weight percent based on weight of the reaction medium in which the HCN and formaldehyde are added.

The reaction medium thus contains the reaction product of the amine/glycolonitrile reaction, formaldehyde, hydrogen cyanide, preferably water, and acid. Use of a solvent other than water is optional, although not preferred. Such optional solvents include methanol, ethanol, or other aliphatic alcohols with four or fewer carbon atoms and the like. Water is preferred because most aminoacetonitrile products are at least partially soluble in organic solvents, and such solubility impairs their isolation by precipitation. However, such solvents are suitable when other isolation methods within the skill in the art, such as evaporation of solvent, are used.

The following examples are offered to illustrate, but not to limit the present invention. All parts, percentages, and ratios are by weight unless stated otherwise. Examples of the invention (Ex) are designated numerically, while comparative samples (C.S.) are designated alphabetically.

COMPARATIVE SAMPLE A

REACTION OF HYDROGEN CYANIDE AND FORMALDEHYDE WITH ETHYLENE DIAMINE

Ethylenediamine (EDA), 0.623 grams (about 98 percent pure) (0.01 moles), is added to a 3-dram vial containing a magnetic stir bar. Water is added to make a total of 1.943 grams. The vial is capped with a septum, and a small balloon is used to prevent escape of gases from the reaction system and allow for pressure equalization. The contents of the vial are continuously stirred and heated at 60° C. Then 1.63 grams 37 percent by weight formaldehyde (0.02 moles) and 0.63 grams 90 percent by weight HCN in water (0.021 moles) are added simultaneously over a 2 hour period via syringes using a syringe pump. The pH is adjusted to about 5.4 with sulfuric acid and an additional 1.62 grams 37 percent formaldehyde and 0.64 grams of 90 percent HCN are added over a two hour period at 60° C. During the addition of the second half of the HCN and formaldehyde, a precipitate is observed. The quantity of precipitate increases as the addition continues. After the addition is complete, the heat is maintained for another 2 hours, after which the stirring is continued at room temperature for about 12 hours. The precipitate (solids) is filtered, washed with a minimum amount of water, dried and weighed. Yield to ethylenediamine tetraacetonitrile (EDTN) (identified by melting point, hydrogen Nuclear Magnetic Resonance ($^1$H NMR), and Carbon 13 Nuclear Magnetic Resonance ($^{13}$C NMR)) based on moles of EDA is 26 percent. The product is dissolved in hexadeutero methyl sulfoxide. The standard for $^1$H NMR is Dioxane, and peaks at 2.71 ppm and 3.83 ppm from that standard are indicative of EDTN. The standard for $^{13}$C NMR is Dioxane and peaks at 42.1, 49.2 and 115.9 ppm from that standard are indicative of EDTN.

EXAMPLE 1

REACTION OF GLYCOLONITRILE WITH EDA AND SUBSEQUENT REACTION WITH FORMALDEHYDE AND HYDROCYANIC ACID

In an apparatus as used in Comparative Sample A, 2.85 grams of 40 percent by weight aqueous glycolonitrile (0.02 moles) is added over 2 hours to 0.01 moles EDA in water at 60° C. while stirring. The reaction product of two equivalents of aqueous glycolonitrile with ethylenediamine is shown to be ethylenediamine diacetonitrile (EDDN) by proton and carbon NMR. The dinitrile intermediate was analyzed just after the addition of the glyconitrile was complete, showing by proton NMR (in D$_2$O solvent) singlets at 3.49 ppm for the acetonitrile methylene protons and 2.64 ppm for the EDA methylene protons. By carbon NMR (in D$_2$O solvent), peaks are at 121.49 ppm for the nitrile carbons, 54.45 ppm for the acetonitrile methylenes and 38.94 ppm for the EDA methylenes. The pH is adjusted to about 5.4 using sulfuric acid. A sample of 1.63 grams of 37 percent formaldehyde (0.02 moles) and 0.61 grams of 90 percent HCN (0.02 moles) are added simultaneously over 2 hours at 60° C. Early into the addition of the HCN and formaldehyde, a precipitate is observed which increases as the addition continues. Heat is continued for 2 hours after the addition is complete and stirring is continued at room temperature for about 12 more hours. The precipitate (solids) is filtered, washed, dried and weighted. Yield to EDTN (identified as in Comparative Sample A) based on EDA is 74 percent.

The EDTN thus prepared is then hydrolyzed by slurrying the solid EDTN and adding the slurry to a heated solution of 40% sodium hydroxide. Hydrolysis processes are well described in the art.

The hydrolysis produces an approximately 40% active (by weight) solution of the tetrasodium salt of ethylenediamine tetraacetic acid (EDTA) which contains less than 0.1% of the following co-products:
nitrilotriacetic acid, Na salt
glocolic acid, Na salt
ethylenediamine monoacetic acid, Na salt
ethylenediamine diacetic acid, Na salt.

COMPARATIVE SAMPLE B

REACTION OF GLYCOLONITRILE WITH ETHYLENEDIAMINE

The process of Example 1 is repeated using 2.85 grams of 40 percent glycolonitrile and 0.61 grams of EDA in water at 60° C. added over a 2 hour period. Following adjustment of pH to about 5.4, another 2.85 grams of 40 percent glycolonitrile is added over a 2 hour period at 60° C. Heat is continued for an additional 2 hours and stirring is maintained at room temperature for an additional 12 hours beyond the heating. Solids of EDTN are isolated as in Example 1 in 13 percent yield. (Solids are not observed until after stirring for some time at room temperature.)

EDTN, $C_{10}H_{12}N_6$, shows three types of carbons by $^{13}C$ NMR, and two types of protons by $^1H$ NMR as described in Comparative Sample A. Melting point is about 129° C.

Comparison of the yields of EDTN in Example 1 (74 percent), and Comparative Samples A (26 percent) and B (13 percent) show that a much greater yield is obtained when glycolonitrile is reacted with a primary amine, and the resulting product is reacted with formaldehyde and HCN under acidic conditions in contrast to the amine reaction with either formaldehyde and HCN alone or glycolonitrile alone.

What is claimed is:

1. A process for preparing aminoacetonitriles comprising the steps of (a) reacting by contacting in a liquid aqueous reaction medium, at a basic pH and at a temperature of from about 0° C. to about 70° C. glycolonitrile with an unsubstituted or inertly-substituted amine having at least one primary amine group to form a intermediate aminonitrile, (b) placing the reaction product of Step (a) in a suitable acidic liquid reaction medium at a temperature of from about 0° C. to about 90° C. and thereafter admixing it with formaldehyde and hydrocyanic acid such that each hydrogen on an amine nitrogen is replaced by an acetonitrile group.

2. A process for preparing ethylenediamine tetraacetonitrile comprising the steps of (a) reacting by contacting in a liquid aqueous reaction medium, at a pH of about 8 to about 13 and at a temperature of from about 0° C. to about 70° C., about two equivalents of glycolonitrile with one equivalent of ethylenediamine to form an intermediate ethylenediamine diacetonitrile, (b) forming an acidic mixture of said intermediate ethylenediamine diacetonitrile in a suitable liquid reaction medium at a temperature of from about 0° C. to about 90° C. and (c) adding about two equivalents of formaldehyde and about two equivalents of hydrocyanic acid to the acidic mixture.

3. The process of claim 1 wherein the ratio of equivalents of glycolonitrile to equivalents of primary and secondary amine is from about 0.95 to about 0.99.

4. The process of claim 1 wherein the pH of the liquid reaction medium in step (a) is about 9 to 12.

5. The process of claim 1 wherein step (a) takes place at a temperature of from about 10° C. to about 60° C.

6. The process of claim 1 wherein step (a) takes place at a temperature of from about 30° C. to about 60° C.

7. The process of claim 5 wherein the ratio of equivalents of glycolonitrile to equivalents of primary and secondary amine is from about 0.95 and about 0.99.

8. The process of claim 1 wherein step (b) takes place at a pH of less than about 5.

9. The process of claim 1 wherein step (b) takes place at a pH of from about 0 to about 3.

10. The process of claim 1 wherein step (b) takes place at a pH of about 1.

11. The process of claim 1 wherein in step (b), the formaldehyde and hydrocyanic acid are added simultaneously or substantially simultaneously.

12. The process of claim 8 wherein the hydrocyanic acid is added at a rate approximately equal to the rate at which it is reacted.

13. The process of claim 1 wherein step (b) takes place at a temperature of from about 0° C. to about 70° C.

14. The process of claim 1 wherein step (b) takes place at a temperature of from about 30° C. to about 70° C.

15. The process of claim 1 wherein said aminoacetonitrile is recovered by filtration.

16. The process of claim 2 wherein the ratio of equivalents of glycolonitrile to equivalents of ethylenediamine is from about 1.90 to about 1.98.

17. The process of claim 2 wherein the pH of the liquid reaction medium in step (a) is about 9 to 12.

18. The process of claim 2 wherein step (a) takes place at a temperature of from about 10° C. to about 60° C.

19. The process of claim 2 wherein step (a) takes place at a temperature of from about 30° C. to about 60° C.

20. The process of claim 18 wherein the ratio of equivalents of glycolonitrile to equivalents of ethylenediamine is from about 1.90 to about 1.98.

21. The process of claim 2 wherein step (b) takes place at a pH of less than about 5.

22. The process of claim 2 wherein step (b) takes place at a pH of from about 0 to about 3.

23. The process of claim 2 wherein step (b) takes place at a pH of about 1.

24. The process of claim 2 wherein in step (b), the formaldehyde and hydrocyanic acid are added simultaneously or substantially simultaneously.

25. The process of claim 21 wherein the hydrocyanic acid is added at a rate approximately equal to the rate at which it is reacted.

26. The process of claim 2 wherein step (b) takes place at a temperature of from about 0° C. to about 70° C.

27. The process of claim 2 wherein step (b) takes place at a temperature of from about 30° C. to about 70° C.

28. The process of claim 2 wherein said ethylenediamine tetraacetonitrile is recovered by filtration.

* * * * *